United States Patent [19]
Zierdt

[11] 4,410,630
[45] Oct. 18, 1983

[54] LYSIS FILTRATION CULTURE CHAMBER

[75] Inventor: Charles H. Zierdt, Rockville, Md.

[73] Assignee: The United States of America as represented by the Department of Health and Human Services, Washington, D.C.

[21] Appl. No.: 330,020

[22] Filed: Dec. 11, 1981

[51] Int. Cl.³ .............................................. C12M 3/00
[52] U.S. Cl. .................................. 435/284; 422/294; 422/296
[58] Field of Search ................. 435/284; 422/294-296

[56] References Cited

U.S. PATENT DOCUMENTS

| | | | |
|---|---|---|---|
| 3,874,851 | 4/1975 | Wilkins et al. | 73/425.6 |
| 4,063,460 | 12/1977 | Svensson | 73/425.6 |
| 4,119,125 | 10/1978 | Elkins | 141/11 |
| 4,142,856 | 3/1979 | Acuff | 422/101 |
| 4,150,950 | 4/1979 | Tageguchi et al. | 422/102 |
| 4,185,964 | 1/1980 | Lancaster | 424/11 |
| 4,220,715 | 9/1980 | Ahnell | 435/289 |
| 4,252,538 | 2/1981 | Barr | 422/102 |

FOREIGN PATENT DOCUMENTS 2435524 5/1980 France ................................ 435/284

OTHER PUBLICATIONS

"Development of a Lysis-Filtration Blood Culture Technique" Journal of Clinical Microbiology, Jan. 1977, pp. 46-50.

Primary Examiner—Ferris H. Lander
Attorney, Agent, or Firm—Browdy & Neimark

[57] ABSTRACT

An apparatus for blood sample treatment involves lysis, filtration and culture, the apparatus being in the form of a unitary culture chamber assembly consisting of an upper chamber for receiving a blood sample, this upper chamber receiving lysing solution squeezed from an attached bag which is subsequently detached. The upper chamber is located over and is in telescopic engagement with a lower chamber having a pointed hollow needle engageable through a rubber diaphragm in the bottom of the upper chamber when the upper chamber is pressed down. This is done after complete blood lysis, and then vacuum is applied to the lower chamber to accomplish filtration. The lower chamber is then detached and discarded. The diaphragm is sealingly covered and an attached bag of culture medium is squeezed to introduce the medium into the upper chamber from the bag. This second bag is detached, leaving the upper chamber as a complete blood culture system.

15 Claims, 4 Drawing Figures

LYSIS FILTRATION CULTURE CHAMBER

FIELD OF THE INVENTION

This invention relates to apparatus for blood sample treatment, and more particularly to a unitary blood culture chamber assembly for performing a process involving the lysis, filtration and culture of a blood sample.

BACKGROUND OF THE INVENTION

In recent years an improved lysis-filtration blood culture process has been developed. A typical process of this kind is described in Zierdt et al., "Development of a Lysis-Filtration Blood Culture Technique", Journal of Clinical Microbiology, January 1977, p. 46-50, which publication is hereby included by reference.

According to the previously employed procedures, the lysis, filtration and culture are performed in separate containers as separate operations. This invites contamination, because of the many operations open to the air, pouring of the mixture from one vessel to another, and transfer of the filter membrane from the filter holder to the final culture bottle. A unitary culture chamber assembly, as described herein, would obviate almost all of this contamination risk.

SUMMARY OF THE INVENTION

In accordance with the present invention, a blood sample is subjected to (1) lysis, (2) filtration, and (3) culturing, in a unitary culture chamber assembly comprising an upper chamber for receiving the blood sample, this upper chamber receiving lysing solution squeezed from an attached flexible bag which is subsequently detached, the upper chamber having a bottom filter membrane with a bottom spout there below. The upper chamber is telescopically engaged with and normal located over a lower chamber having an upwardly-directed hollow needle engageable through a rubber diaphragm in the bottom spout of the upper chamber when said upper chamber is pressed down, which is done after complete blood lysis. After this, vacuum is applied to the lower chamber to accomplish filtration. The lower chamber, containing the filtrate, is then slidably disengaged from the upper chamber and discarded. The bottom spout is sealingly covered by a cap, and an attached flexible bag of culture medium is squeezed to introduce the medium into the upper chamber from the bag. The second bag is detached, leaving the upper chamber as a complete blood culture system.

The above-described improved unitary system provides superio performance in that the phagocytes of the blood are killed and lysis releasing bacteria that would otherwise be killed by phagocytic action. Other possible advantages are the removal from the blood culture of antibiotics, if present in the patient's blood. Also removed via the filtrate, which is discarded, are antibodies, complement, and opsonins. In other words, the removal is accomplished of all the anti-bacterial mechanisms of whole blood. Remaining on the filter membrane, which is then cultured, are red blood cell membranes, white blood cell membranes and nucleii, platelets, and such microorganisms which happen to be present. Although the system will trap mycoplasma and chlamydia, the bulk of microorganisms cultured are bacteria and fungi.

Accordingly, an object of the invention is to provide for improved blood sample treatment which overcomes the deficiencies and disadvantages of systems previously employed for such treatment.

A further object of the invention is to provide an improved unitary apparatus for blood sample treatment which enables the performance of blood lysis, filtration and culture in a simple and efficient manner, with minimum risk of contamination.

A still further object of the invention is to provide an improved unitary blood culture chamber assembly containing all the necessary structural elements for performing blood lysis, filtration and culture, which is relatively compact in size, which is easy to manipulate, and which enables a blood culture process to be accomplished with high efficiency and with low contamination risk.

A still further object of the invention is to provide an improved unitary blood culture chamber assembly which includes means for efficiently performing lysis of a blood sample in a main chamber, establishing communication with a vacuum filter chamber which can be subsequently removed, and for subsequently establishing the main chamber as a complete blood culture system, whereby a blood sample culture treatment can be carried out in an efficient and reliable manner.

A still further object of the invention is to provide an improved unitary apparatus for blood sample treatment which is in the form of a self-contained, easily manipulated combination of all the elements required for carrying out lysis, filtration and bacterial culture of a blood sample, and which destroys and removes phagocytes, antibodies, antibiotics, and other anti-bacterial undesired blood components, leaving red blood cell membranes, which blood cell membranes and nucleii, platelets, and such other microorganisms which happen to be present, thereby enabling efficient and reliable culture, with minimum risk of contamination of a blood sample from a patient.

BRIEF DESCRIPTION OF THE DRAWINGS

Further objects and advantages of the invention will become apparent from the following description and claims, and from the accompanying drawings, wherein:

DETAILED DESCRIPTION OF A PREFERRED EMBODIMENT

Figure 1:
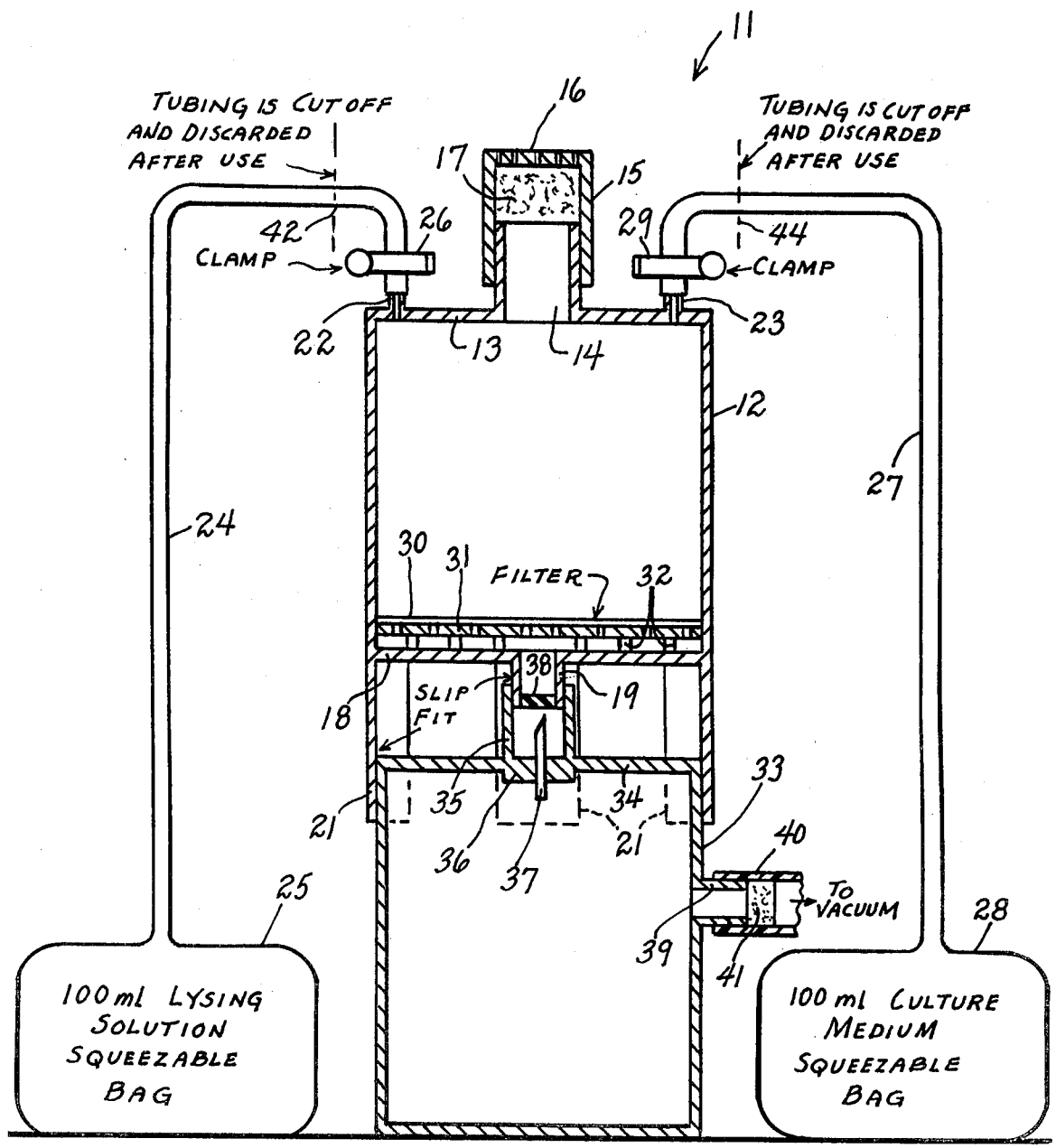
FIG. 1 is a vertical cross-sectional view taken through a typical blood sample treatment apparatus according to the present invention.

Referring to the drawings, 11 generally designates an improved blood sample treatment apparatus constructed in accordance with the present invention. The apparatus 11 comprises an upper chamber 12 which may be substantially cylindrical in shape and has a top wall 13 with an upwardly directed inlet conduit 14 normally covered by a removable cap 15 with a perforated top wall 16. The cap 15 is provided internally with a mass of porous filter material 17 which is coextensive with and located subjacent to the top wall 16, as shown in FIG. 1. Cap 15 is readily removable to allow injection of a blood sample to be processed.

Figure 2:
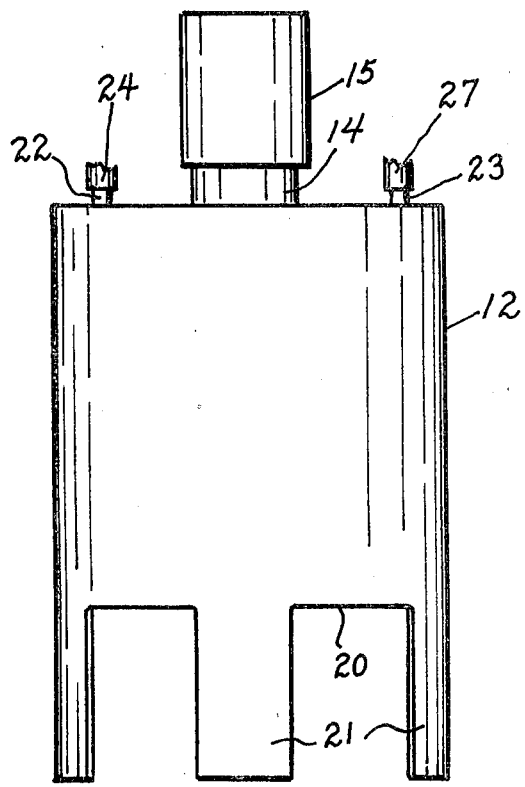
FIG. 2 is a front elevational view of the upper chamber forming part of the apparatus of FIG. 1.
Figure 3:
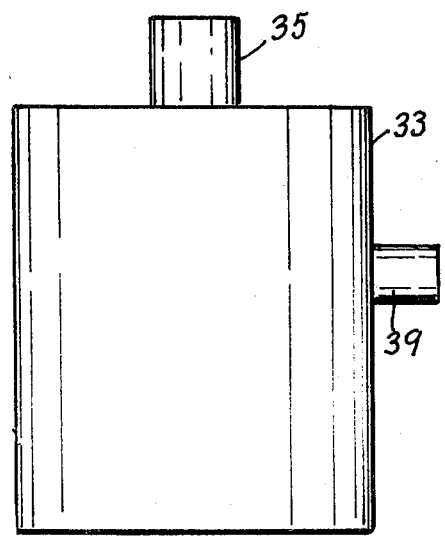
FIG. 3 is a front elevational view of the lower chamber of the apparatus of FIG. 1.

Upper chamber 12 has a bottom wall 18 formed with a central depending spout 19. The portion of the cylindrical wall of upper chamber 12 extending below the bottom wall 18 is notched out at 20 to define four evenly spaced depending supporting legs 21 of substantial length, as shown in FIGS. 1 and 2. Top wall 13 is formed with opposite upstanding inlet conduits 22 and 23. Conduit 22 is connected to a flexible plastic conduit 24 leading to a flexible bag 25 containing lysing solution, such as 0.01 M sodium phosphate buffer of pH 9.0, with 0.7% Tween 2 C and 0.5% Rhozyme P 11. Other known lysing solutions may be used, such as 0.1% Triton X-100 in 0.01 M $NaHCO_3$-$Na_2CO_3$ buffer, with 3% of stock Rhozyme 41 solution, as described in the above-cited Journal of Clinical Microbiology publication.

The conduit 24 is normally closed off by a heat seal (weld) located adjacent to the chamber inlet conduit 22. The opposite conduit 23 is connected to a flexible plastic conduit 27 leading to a flexible bag 28 containing culture medium. The culture medium may be similar to that described in the above-cited Journal of Microbiology publication, or may be any other suitable culture material.

Conduit 27 is normally closed off by a conventional clamp 2 located adjacent to the chamber inlet conduit 23.

A filter membrane 30 of suitable porosity, for example, about 0.6 μM pore membrane, is supported on a perforated disc 31 having depending short spacer pins 32 supportingly engaging bottom wall 18.

Figure 4:
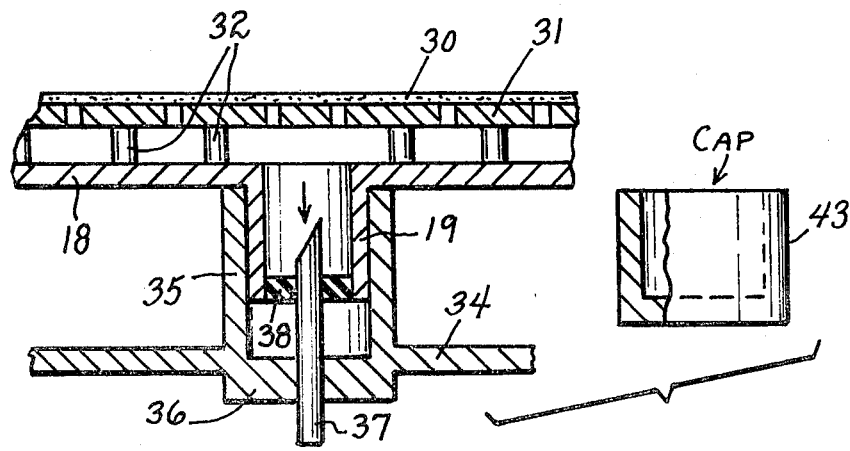
FIG. 4 is an enlarged fragmentary vertical cross-sectional view of the central portion of the apparatus of FIG. 1 after the upper chamber has been pushed down to communicatively connect the bottom spout of the upper chamber to the lower chamber by the penetration of the upper chamber diaphragm member by the hollow needle of the lower chamber, and showing the sealing cap used to subsequently cover the bottom spout.

A cylindrical bottom chamber 33 is slidably and snugly received telescopically within the arcuately contoured inner surface of the legs 21. Chamber 33 has a top wall 34 formed with a central upwardly extending cup 35 whose bottom wall 36 has rigidly embedded therein a vertical pointed hollow needle 37. Cup 35 slidably and snugly telescopically receives the depending spout 19. A rubber diaphragm 38 is sealingly secured in the bottom rim portion of spout 19, and is normally spaced a short distance above the pointed top end of needle 37, the spacing being maintained by the frictional engagement of legs 21 with chamber 33 and spout 19 with the inside surface of cup 35. By exerting manual downward force on upper chamber 12, with lower chamber 33 held stationary, said upper chamber may be sufficiently depressed so as to force needle 37 through the rubber diaphragm 38 and thereby communicatively connect upper chamber 12 with lower chamber 33, as shown in FIG. 4.

Lower chamber 33 has a side conduit 39 connected to a conduit 40 which may be at times connected to a suitable vacuum source. The connection of conduit 40 to conduit 39 includes a mass 41 of suitable filter material.

The entire apparatus 11 should be normally enclosed in a clear plastic bag, and should be suitably sterilized, such as by ethylene oxide gas, or by means of a gamma particle generator.

The following steps may be employed in the use of the lysis filtration blood culture apparatus 11:

1. The apparatus 11 is kept on hand in the hospital ward.

2. At the time of phlebotomy, the apparatus 11 is removed from its protective container. The clamp 26 is released on the tubing 24 leading to the bag 25 of lysing solution, which is squeezed into the upper chamber 12. The clamp 26 is then reapplied to seal tube 24 and the tubing 24 is then out off above the clamp 26, as shown at 42.

3. The top cap 15 is slipped off. From 5 to 10 ml of the patient's blood is injected into the upper chamber 12 via conduit 14. The top cap 15 is replaced, and the chamber is swirled to mix the blood and lysing solution.

4. The culture apparatus 11 (minus the bag 25) is sent to the laboratory.

5. After incubation for one hour, to permit complete blood lysis, the upper and lower chambers 12 and 33 are pressed together so that the needle 37 of the lower chamber penetrates the diaphragm 38 of the upper chamber substantially to a position shown in FIG. 4.

6. Vacuum is applied to the conduit 40, causing filtration through the filter membrane 30. Filtration requires only a few seconds.

7. The lower chamber 33 is pulled free and discarded, said lower chamber containing the filtrate resulting from the suction step. Remaining on the filter membrane 30 are red blood cell membranes, white blood cell membranes and nucleii, platelets, and microorganisms that happen to be present. The bulk of such microorganisms are bacteria and fungi.

8. A sterile cap 43 (see FIG. 4) is slipped over the bottom spout 19 and sealingly tightened thereon. Said spout is dimensioned to make a tight frictional seal with spout 19.

9. The clamp 29 on the tubing 27 leading to the bag 28 of culture medium is released, and said bag 28 is squeezed so as to force the culture medium into the upper chamber 12. The clamp 29 is again applied and the tubing 27 is cut off upwardly adjacent to the clamp, for example, at 44 in FIG. 1.

10. The upper chamber 12, now a complete blood culture system, is placed in a 35°–37° C. incubator and observed daily for microbial growth.

While the vertically aligned chambers 12 and 33 are shown herein as being substantially cylindrical, they may take other forms than cylindrical, such as being slightly tapered, or having other than circular cross-sectional shapes.

While a specific embodiment of an imporved blood sample treatment apparatus has been disclosed in the foregoing description it will be understood that various modifications within the scope of the invention may occur to those skilled in the art. Therefore it is intended that adaptations and modifications should and are intended to be comprehended within the meaning and range of equivalents of the disclosed embodiment.

What is claimed is:

1. An apparatus for blood sample treatment involving lysis, filtration and culture, said apparatus comprising an upper chamber for receiving a blood sample, a first flexible bag containing lysing solution, a first flexible severable conduit connecting said first flexible bag to the upper chamber, a first removable clamp on said first flexible conduit, a second flexible bag containing culture medium, a second flexible severable conduit connecting said second flexible bag to said upper chamber, a second removable clamp on said second flexible conduit, said upper chamber having a bottom wall provided with a depending discharge spout, a filter member mounted in said upper chamber above said bottom wall, a lower chamber below said upper chamber and having a top wall provided with a cup member telescopically engaged with said discharge spout, said discharge spout being provided with a penetrable diaphragm normally sealing the spout, a pointed upstanding hollow needle mounted in said cup member and being arranged to penetrate the diaphragm when the upper and lower chambers are pressed together, to thereby communicatively connect the chamber, vacuum conduit means connected to said lower chamber, and wherein said penetrable diaphragm is sealingly secured in the bottom rim portion of said discharge spout.

2. The blood sample treatment apparatus of claim 1, and depending means on the upper chamber slidably and retentively engaging the outer surface of the lower chamber.

3. The blood sample treatment apparatus of claim 2, and wherein said depending means comprises a plurality of spaced leg elements depending from said upper chamber.

4. The blood sample treatment apparatus of claim 3, and wherein said lower chamber has a convexly curved outer contour and said leg elements are arcuately shaped to telescopically engage said lower chamber.

5. The blood sample treatment apparatus of claim 1, and wherein said upper chamber is provided with a perforated rigid filter supporting plate-like member having depending spacer means engaging the bottom wall of the upper chamber, said filter member comprising a filter membrane supported on said perforated plate-like member.

6. The blood sample treatment apparatus of claim 5, and wherein said depending spacer means comprises a plurality of rigid pin elements depending from said plate-like member.

7. The blood sample treatment apparatus of claim 1, and wherein said discharge spout depends substantially centrally from said upper chamber bottom wall.

8. The blood sample treatment apparatus of claim 1, and wherein said upper chamber is formed with a plurality of spaced depending leg elements which are telescopically engaged with the outer surface of said lower chamber and substantially conform with the contour of said lower chamber.

9. The blood sample treatment apparatus of claim 1, and wherein said vacuum conduit means is connected to a side wall portion of said lower chamber.

10. The blood sample treatment apparatus of claim 1, and wherein said upper and lower chambers are substantially in vertical alignment.

11. The blood sample treatment apparatus of claim 10, and wherein the peripheral wall of the upper chamber is formed with a plurality of spaced downward extensions defining supporting legs, said downward extensions being slidably and snugly telescopically engaged with the lower chamber.

12. An apparatus for blood sample treatment involving lysis, filtration and culture, said apparatus comprising an upper chamber for receiving a blood sample, a first flexible bag containing lysing solution, a first flexible severable conduit connecting said first flexible bag to the upper chamber, a first removable clamp on said first flexible conduit, a second flexible bag containing culture medium, a second flexible severable conduit connecting said second flexible bag to said upper chamber, a second removable clamp on said second flexible conduit, said upper chamber having a bottom wall provided with a depending discharge spout, a filter member mounted in said upper chamber above said bottom wall, a lower chamber below said upper chamber and having a top wall provided with a cup member telescopically engaged with said discharge spout, said discharge spout being provided with a penetrable diaphragm normally sealing the spout, a pointed upstanding hollow needle mounted in said cup member and being arranged to penetrate the diaphragm when the upper and lower chambers are pressed together, to thereby communicatively connect the chambers, vacuum conduit means connected to said lower chamber, and wherein said upper chamber is provided with a perforated rigid filter supporting plate-like member having depending spacer means engaging the bottom wall of the upper chamber, said filter member comprising a filter membrane supported on said perforated plate-like member.

13. The blood sample treatment apparatus of claim 12, and wherein said depending spacer means comprises a plurality of rigid pin elements depending from said plate-like member.

14. An apparatus for blood sample treatment involving lysis, filtration and culture, said apparatus comprising an upper chamber for receiving a blood sample, a first flexible bag containing lysing solution, a first flexible severable conduit connecting said first flexible bag to the upper chamber, a first removable clamp on said first flexible conduit, a second flexible bag containing culture medium, a second flexible severable conduit connecting said second flexible bag to said upper chamber, a second removable clamp on said second flexible conduit, said upper chamber having a bottom wall provided with a depending discharge spout, a filter member mounted in said upper chamber above said bottom wall, a lower chamber below said upper chamber and having a top wall provided with a cup member telescopically engaged with said discharge spout, said discharge spout being provided with a penetrable diaphragm normally sealing the spout, a pointed upstanding hollow needle mounted in said cup member and being arranged to penetrate the diaphragm when the upper and lower chambers are pressed together, to thereby communicatively connect the chambers, vacuum conduit means connected to said lower chamber, and wherein said upper chamber is formed with a plurality of spaced depending leg elements which are telescopically engaged with the outer surface of said lower chamber and substantially conform with the contour of said lower chamber.

15. An apparatus for blood sample treatment involving lysis, filtration and culture, said apparatus comprising an upper chamber for receiving a blood sample, a first flexible bag containing lysing solution, a first flexible severable conduit connecting said first flexible bag to the upper chamber, a first removable clamp on said first flexible conduit, a second flexible bag containing culture medium, a second flexible severable conduit connecting said second flexible bag to said upper chamber, a second removable clamp on said second flexible conduit, said upper chamber having a bottom wall provided with a depending discharge spout, a filter member mounted in said upper chamber above said bottom wall, a lower chamber below said upper chamber and having a top wall provided with a cup member telescopically engaged with said discharge spout, said discharge spout being provided with a penetrable diaphragm normally sealing the spout, a pointed upstanding hollow needle mounted in said cup member and being arranged to penetrate the diaphragm when the upper and lower chambers are pressed together, to thereby communicatively connect the chambers, vacuum conduit means connected to said lower chamber, wherein said upper and lower chambers are substantially in vertical alignment, and wherein the peripheral wall of the upper chamber is formed with a plurality of spaced downward extensions defining supporting legs, said downward extensions being slidably and snugly telescopically engaged with the lower chamber.

* * * * *

UNITED STATES PATENT AND TRADEMARK OFFICE
CERTIFICATE OF CORRECTION

PATENT NO. : 4,410,630
DATED : October 18, 1983
INVENTOR(S) : Charles H. ZIERDT

It is certified that error appears in the above-identified patent and that said Letters Patent are hereby corrected as shown below:

Column 1, line 62, "nucleii" should read --nuclei--
Column 2, line 33, "which" should read --white--
Column 4, line 26, "nuceii" should read --nuclei--

Signed and Sealed this

Seventh Day of August 1984

[SEAL]

Attest:

GERALD J. MOSSINGHOFF

Attesting Officer  Commissioner of Patents and Trademarks